United States Patent [19]

Hamashima et al.

[11] 4,197,402
[45] Apr. 8, 1980

[54] CEPHALOSPORIN ANALOGUES

[75] Inventors: Yoshio Hamashima, Kyoto; Wataru Nagata, Nishinomiya, both of Japan

[73] Assignee: Shionogi & Co., Ltd., Osaka, Japan

[21] Appl. No.: 15,180

[22] Filed: Feb. 26, 1979

Related U.S. Application Data

[63] Continuation-in-part of Ser. No. 820,032, Jul. 28, 1977, abandoned.

[30] Foreign Application Priority Data

Aug. 9, 1976 [JP] Japan ................................ 51-95146

[51] Int. Cl.² ............................................. C07D 498/00
[52] U.S. Cl. ................................. 544/90; 424/248.51; 424/248.54
[58] Field of Search ............................................. 544/90

[56] References Cited

U.S. PATENT DOCUMENTS

| | | | |
|---|---|---|---|
| 3,992,377 | 11/1976 | Chauvette et al. | 424/246 X |
| 4,013,653 | 3/1977 | Wolfe | 544/92 |
| 4,052,554 | 10/1977 | Breuer et al. | 544/26 |

FOREIGN PATENT DOCUMENTS

| | | | |
|---|---|---|---|
| 857482 | 2/1978 | Belgium | 544/90 |
| 857621 | 2/1978 | Belgium | 544/90 |
| 50-50394 | 6/1975 | Japan | 544/90 |
| 51-41385 | 7/1976 | Japan | 544/90 |

OTHER PUBLICATIONS

Firestone et al., J. Med. Chem. vol. 20, pp. 551 to 556 (April 1977).
Kim et al., Tetrahedron Letters, 1978, pp. 409 to 412.
Lednicer et al., The Organic Chemistry of Drug Synthesis, pp. 408 to 422, John Wiley and Sons, NY (1977).
Moll et al., Archiv der Pharmazie, vol. 308, pp. 483–489 (1975) Chemical Abstracts, vol. 81, abst. 37560f (1974) (abst. of Ger. Offen. 2,355,209).

*Primary Examiner*—John D. Randolph
*Attorney, Agent, or Firm*—Wenderoth, Lind & Ponack

[57] ABSTRACT

1-Oxa-cephalosporin analogues of the formula:

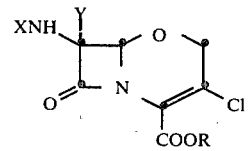

[wherein
X is 3-thienylmalonyl, phenylmalonyl, 4-hydroxyphenylmalonyl, or 2-fluoro-4-hydroxyphenylmalonyl;
Y is hydrogen or methoxy; and
R is hydrogen, alkali metal, or alkaline earth metal]
and the preparation thereof.

10 Claims, No Drawings

CEPHALOSPORIN ANALOGUES

This application is a continuation of Ser. No. 820,032 filed July 28, 1977, now abandoned.

This invention relates to 1-oxadethia-3-cephem compounds and salts thereof. Particularly, this invention relates to 3-chloro-7-acylamino-1-oxa-1-dethia-3-cephem-4-carboxylic acids or salts thereof. Compounds of this invention are represented by the formula:

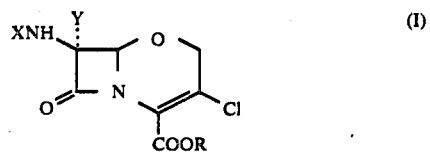

wherein
X is 3-thienylmalonyl, phenylmalonyl, 4-hydroxyphenylmalonyl, or 2-fluoro-4-hydroxyphenylmalonyl;
Y is hydrogen or methoxy; and
R is hydrogen, alkali metal, or alkaline earth metal.

The compounds in this invention represented by the formula (I) may be prepared on acylation of the corresponding 7-amino derivatives represented by the following formula (II). The reaction sequence is represented as follows:

Reaction Scheme 1

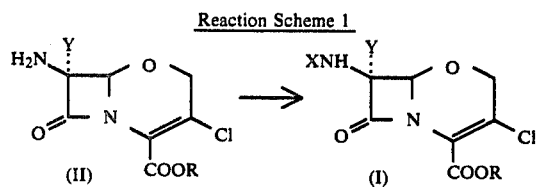

(wherein X, Y, and R are the same as mentioned above).

The starting materials represented by the general formula (II) may be prepared from well-known compounds of the formula (a)(Japanese Unexamined Patent Publication No. 51-41385) in a manner as shown in Reaction Scheme 2. In Reaction Scheme 2, X' is amino protecting group; and Y and R are the same as mentioned above.

Reaction Scheme 2

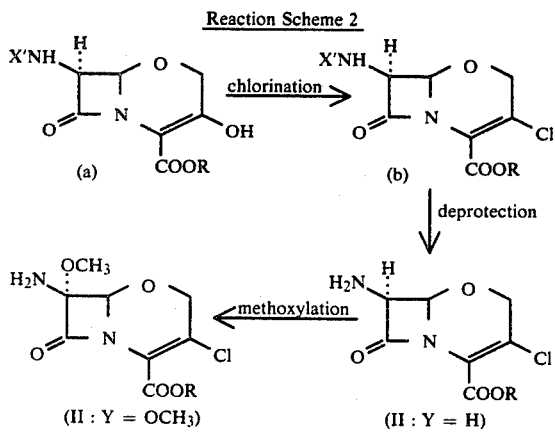

Each reaction step illustrated in Reaction Scheme 2 is briefly explained as follows.

The reaction of the starting materials (a) to (b) is chlorination of the 3-hydroxy group (enolic hydroxy group), by which chloro is introduced into the 3-position. Removal of the amino protecting group X' from the intermediates (b) yields the starting materials (II), wherein Y is hydrogen.

Introduction of methoxy group into the starting materials (II) (Y=H) in a well-known manner, for example, in a manner as described in Japanese Unexamined Patent Publication No. 50-50394 yields the other starting materials (II)(X=OCH$_3$).

Acylation at the 7-amino as shown in Reaction Scheme 1 may be carried out in accordance with acylation procedure ordinarily used in the field of penicillin and cephalosporin chemistry. Representative of acylating agents are the carboxylic acids (i.e. X'COOH) corresponding to desired acyl group X (i.e. X'—CO) or their reactive derivatives such as acid halides, acid anhydrides (mixed acid anhydrides are included), esters, azides, imidazolides, pyrazolides, triazolides, and the like. All of the above-mentioned acylating agents may be employed in acylation in well-known manners. The following exemplifies the particularly preferred acylation with free carboxylic acids and acid halides.

The acylation at the 7-amino with free carboxylic acids, X'—COOH, as acylating agents is preferably carried out in the presence of carbodiimides such as DCC (N,N'-dicyclohexylcarbodiimide) in a solvent such as methylene chloride, acetonitrile, dimethylformamide, pyridine, tetrahydrofuran and the like at room temperature or below.

When acid halides, in particular, acid chlorides or acid bromides are employed, the acylation is preferably carried out in an inert solvent under coolng at low temperature. Preferred inert solvents are aprotic solvents such as benzene, ethers, methylene chloride, chloroform, and the like.

In carrying out these reactions, it is appropriate to properly protect easily attacked groups, for example, when R is hydrogen in the starting compounds (II) or when the acylating agents have hydroxy, carboxy group or the like. Introduction and elimination of the protecting groups may be carried out in a conventional procedure.

It has been confirmed by in vitro assay method that the objective compounds (I) in this invention exhibit potent antimicrobial activity against gram-positive and negative bacteria. They show much more potent antimicrobial activity than the corresponding cephalosporin congeners against some gram-negative bacterial strains e.g. β-lactamase resistant *Escherichia coli* and *Klebsiella pneumoniae*. They may be applied in prevention and treatment of various infections caused by those bacteria. For example, these compounds may be administered to human intravenously at a dose of 500 mg–5 g a day or by other suitable manners (e.g. oral administration, external application), for purpose of prevention and treatment of infections.

The pharmaceutical compositions of this invention may contain 0.01% to 99% by weight of Compound (I) as an active ingredient. For example, a vial preparation and external ointment containing an effective amount of Compound (I) each may be produced by dissolving or suspending in a suitable solvent (e.g. water for injection) and mixing with hydrophilic ointment base (e.g. macrogol) just before use.

Thus, a human or veterinary bacterial infection as above caused by a bacteria sensitive to Compound (I)

may be treated by administering an effective amount of the said compound enterally or parenterally.

EXAMPLE 1

3-Chloro-7β-phenylmalonamido-1-oxa-1-dethia-3-cephem-4-carboxylic acid (1) To a suspension of 40 mg of 3-chloro-7β-amino-1-oxa-1-dethia-3-cephem-4-carboxylic acid in 3 ml of acetonitrile is added 82 μl of O,N-bis(trimethylsilyl)acetamide, and the mixture is stirred at room temperature for 145 minutes under nitrogen atmosphere. N-Methylmorpholine (28 μl) and a methylene chloride solution of acid chloride prepared from 95 mg of phenylmalonic acid diphenylmethyl monoester, 38 μl of triethylamine and 23 μl of oxalyl chloride are added thereto. The mixture is stirred at room temperature for 20 minutes, poured into 3% phosphoric acid and extracted with ethyl acetate. The extract is washed with water, dried over sodium sulfate and treated with chromatography (silica gel containing 10% water/ethyl acetate-acetic acid (50:1)) to yield 88 mg of 3-chloro-7β-(α-benzhydryloxycarbonyl)phenylacetamido-1-oxa-1-dethia-3-cephem-4-carboxylic acid (88% yield).

(2) To a solution of 83 mg of the above obtained product in 2 ml of methylene chloride are added 0.2 ml of anisole and 0.2 ml of trifluoroacetic acid, and the mixture is stirred at 0° C. for 75 minutes and evaporated under reduced pressure. The residue is washed with n-hexane and diethyl ether-hexane to yield 50 mg of 3-chloro-7β-phenylmalonamido-1oxa-1-dethia-3-cephem-4-carboxylic acid in 86% yield.

IR: $\nu_{max}^{CHCl_3}$ 1785, 1720, 1670, 1625 cm$^{-1}$.

$[\alpha]_D^{24.5}$ −22.9°±6.5° (c=0.096, CH$_3$OH).

EXAMPLE 2

3-Chloro-7α-methoxy-7β-phenylmalonamido-1-oxa-1-dethia-3-cephem-4-carboxylic acid (1) To a solution of 35 mg (0.091 mmole) of p-nitrobenzyl 3-chloro-7α-methoxy-7β-amino-1-oxa-1-dethia-3-cephem-4-carboxylate dissolved in 3 ml of methylene chloride at −20° C. are added 15 μl (1.5 equivalents) of N-methylmorpholine and 1.5 equivalents of 2-phenyl-2-benzhydryloxycarbonylacetyl chloride, and the mixture is stirred at the same temperature for 1 hour, poured into 5% phosphoric acid aqueous solution under ice cooling and extracted with ethyl acetate. The extract is washed with water, dried and evaporated under reduced pressure. The residue (93 mg) is chromatographed on a column of 5 g of silica gel and eluted with a mixture of benzene and ethyl acetate (10:1) to yield 54 mg of p-nitrobenzyl 3-chloro-7α-methoxy-7β-(α-phenyl-α-benzhydryloxycarbonyl)acetamido-1-oxa-1-dethia-3-cephem-4-carboxylate (83.2% yield).

TLC: Rf=0.30 (benzene:ethyl acetate; 5:1).

IR: $\nu_{max}^{CHCl_3}$ 1795, 1740, 1730, 1695, 1350 cm$^{-1}$.

NMR: $\delta^{CDCl_3}$ 3.40, 3.44(1:1,3H), 4.33(bs,2H), 4.44(s,1H), 5.13(s,1H), 5.43(ABq,2H), 6.97(s,1H), 7.68(d,J=9 Hz,2H), 8.29(d,J=9 Hz,2H).

(2) To a solution of 53 mg of the above product in a mixture of 2.5 ml of methylene chloride and 2.5 ml of acetic acid is added 50 mg of active zinc powder under ice cooling and the mixture is stirred for 50 minutes and then filtered. The filtrate is diluted with methylene chloride, washed with water, dried and evaporated under reduced pressure. The residue (50 mg) is chromatographed on a column of 2.5 g of silica gel containing 10% water and eluted with chloroform-methanol (95:5) to yield 35 mg of 3-chloro-7α-methoxy-7β-(α-phenyl-α-benzhydryloxycarbonyl)acetamido-1-oxa-1-dethia-3-cephem-4-carboxylic acid as powder (81.6% yield).

TLC: Rf=0.32 (ethyl acetate:acetic acid:water=18:1:1).

IR: $\nu_{max}^{KBr}$ 1757, 1702 cm$^{-1}$.

NMR: $\delta^{CDCl_3-CD_3OD}$ 3.42(s,3H), 5.09(bs,1H), 6.94(s,1H).

(3) To a solution of 33 mg of the above product in 1.5 ml of methylene chloride are added 0.2 ml of anisole and 0.2 ml of trifluoroacetic acid and the mixture is stirred for 30 minutes. Then, 5 ml of toluene is added, and the mixture is evaporated under reduced pressure. The residue is washed with petroleum ether to yield 24 mg of 3-chloro-7α-methoxy-7β-phenylmalonamido-1-dethia-1-oxa-3-cephem-4-carboxylic acid as powder.

TLC: Rf=0.52 (ethyl acetate:acetic acid:water=5:1:1)

IR: $\nu_{max}^{KBr}$ 1782, 1705(sh), 1675 cm$^{-1}$.

EXAMPLE 3

According to a manner similar to that of Example 1 or 2, following compounds are prepared:

3-chloro-7β-(3-thienyl)malonamido-1-oxa-1-dethia-3-cephem-4-carboxylic acid;

3-chloro-7α-methoxy-7β-(3-thienyl)malonamido-1-oxa-1-dethia-3-cephem-4-carboxylic acid;

3-chloro-7β-(4-hydroxyphenyl)malonamido-1-oxa-1-dethia-3-cephem-4-carboxylic acid;

3-chloro-7α-methoxy-7β-(4-hydroxyphenyl)-malonamido-1-oxa-1-dethia-3-cephem-4-carboxylic acid;

3-chloro-7β-(2-fluoro-4-hydroxyphenyl)malonamido-1-oxa-1-dethia-3-cephem-4-carboxylic acid; and 3-chloro-7α-methoxy-7β-(2-fluoro-4-hydroxyphenyl)-malonamido-1-oxa-1-dethia-3-cephem-4-carboxylic acid.

EXAMPLE 4

Into a vial containing 1 g of sodium salt of Compound of claim 1 is added 5 ml of sterile water, and the solution is injected intravenously once a day to a patient suffering from renal bacterial infection caused by *Escherichia coli*.

We claim:

1. A compound represented by the formula:

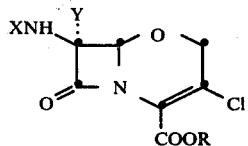

(wherein

X is 3-thienylmalonyl, phenylmalonyl, 4-hydroxyphenylmalonyl, or 2-fluoro-4-hydroxyphenylmalonyl;

Y is hydrogen or methoxy; and

R is hydrogen, alkali metal, or alkaline earth metal.)

2. A compound claimed in claim 1, wherein X is phenylmalonyl.

3. A compound claimed in claim 1, namely 3-chloro-7β-(3-thienyl)malonamido-1-oxa-1-dethia-3-cephem-4-carboxylic acid.

4. A compound claimed in claim 1, namely 3-chloro-7α-methoxy-7β-(3-thienyl)malonamido-1-oxa-1-dethia-3-cephem-4-carboxylic acid.

5. A compound claimed in claim 1, namely 3-chloro-7β-phenylmalonamido-1-oxa-1-dethia-3-cephem-4-carboxylic acid.

6. A compound claimed in claim 1, namely 3-chloro-7α-methoxy-7β-phenylmalonamido-1-oxa-1-dethia-3-cephem-4-carboxylic acid.

7. A compound claimed in claim 1, namely 3-chloro-7β-(4-hydroxyphenyl)malonamido-1-oxa-1-dethia-3-cephem-4-carboxylic acid.

8. A compound claimed in claim 1, namely 3-chloro-7α-methoxy-7β-(4-hydroxyphenyl)malonamido-1-oxa-1-dethia-3-cephem-4-carboxylic acid.

9. A compound claimed in claim 1, namely 3-chloro-7β-(2-fluoro-4-hydroxyphenyl)malonamido-1-oxa-1-dethia-3-cephem-4-carboxylic acid.

10. A compound claimed in claim 1, namely 3-chloro-7α-methoxy-7β-(2-fluoro-4-hydroxyphenyl)-malonamido-1-oxa-1-dethia-3-cephem-4-carboxylic acid.

* * * * *